(12) United States Patent
Ortega et al.

(10) Patent No.: US 7,512,440 B2
(45) Date of Patent: Mar. 31, 2009

(54) VENTRICULAR PACING

(75) Inventors: Daniel Felipe Ortega, Buenos Aires (AR); Alberto German Giniger, Buenos Aires (AR); Qingsheng Zhu, Wexford, PA (US); J. Edward Shapland, Vadnais Heights, MN (US)

(73) Assignee: Action Medical, Inc., Vadnais Height, MN (US)

( * ) Notice: Subject to any disclaimer, the term of this patent is extended or adjusted under 35 U.S.C. 154(b) by 220 days.

(21) Appl. No.: 11/300,611

(22) Filed: Dec. 13, 2005

(65) Prior Publication Data

US 2006/0136001 A1 Jun. 22, 2006

(30) Foreign Application Priority Data

Dec. 20, 2004 (AR) ............................ 20040104782

(51) Int. Cl.
*A61N 1/362* (2006.01)
(52) U.S. Cl. ......................................... 607/9
(58) Field of Classification Search ................ 607/9
See application file for complete search history.

(56) References Cited

U.S. PATENT DOCUMENTS

| | | | |
|---|---|---|---|
| 4,365,639 A | 12/1982 | Goldreyer | |
| H356 H | 11/1987 | Stokes et al. | |
| 4,895,152 A | 1/1990 | Callaghan et al. | |
| 5,174,289 A | 12/1992 | Cohen | |
| 5,181,511 A | 1/1993 | Nickolls et al. | |
| 5,299,569 A | 4/1994 | Wernicke et al. | |
| 5,718,720 A | 2/1998 | Prutchi et al. | |
| 5,769,881 A | 6/1998 | Schroeppel et al. | |
| 5,800,465 A | 9/1998 | Thompson et al. | |
| 6,141,588 A * | 10/2000 | Cox et al. ........... | 607/9 |
| 6,141,594 A | 10/2000 | Flynn et al. | |
| 6,161,029 A | 12/2000 | Spreigl et al. | |
| 6,219,581 B1 | 4/2001 | Schaldach et al. | |
| 6,230,061 B1 | 5/2001 | Hartung | |
| 6,471,697 B1 | 10/2002 | Lesh | |
| 6,542,775 B2 | 4/2003 | Ding et al. | |

(Continued)

OTHER PUBLICATIONS

Furman, et al., "A Practice of Cardiac Pacing," Chapter 5, "Permanent Pacemaker Implantation," pp. 97-127, Futura Publishing Co., Inc., Mount Kisco, NY, USA (1986).

(Continued)

*Primary Examiner*—Carl H Layno
*Assistant Examiner*—Brian T Gedeon
(74) *Attorney, Agent, or Firm*—Crawford Maunu PLLC

(57) ABSTRACT

A method and apparatus are disclosed for treating a condition of a patient's heart includes placing a first electrode and a second electrode in a right ventricle of the heart. A reference electrode is placed within the patient and internal or external to the heart. A pacing signal is generated including a first signal component, a second signal component and a reference component with the first and second signal components having opposite polarity and with both of the first and second components having a potential relative to the reference component. The first component is transmitted to the first electrode. The second component is transmitted to the second electrode. The reference electrode is connected to the reference component which may be an electrical ground. The pacing signal and the placement of the electrodes are selected to alter a contraction of a left ventricle of the heart.

20 Claims, 10 Drawing Sheets

U.S. PATENT DOCUMENTS

| | | | |
|---|---|---|---|
| 6,643,546 | B2 | 11/2003 | Mathis et al. |
| 6,766,190 | B2 | 7/2004 | Ferek-Petric et al. |
| 6,804,555 | B2 | 10/2004 | Warkentin |
| 6,901,289 | B2 | 5/2005 | Dahl et al. |
| 6,907,285 | B2 | 6/2005 | Denker et al. |
| 7,130,682 | B2 * | 10/2006 | Stahmann et al. .............. 607/9 |
| 2002/0169484 | A1 | 11/2002 | Mathis et al. |
| 2002/0193836 | A1 | 12/2002 | Schmidt |
| 2003/0009145 | A1 | 1/2003 | Struijker-Boudier et al. |
| 2004/0006265 | A1 | 1/2004 | Alhussiny |
| 2004/0153127 | A1 | 8/2004 | Gordon et al. |
| 2004/0215249 | A1 | 10/2004 | Corbucci |
| 2005/0125041 | A1 | 6/2005 | Min et al. |
| 2005/0203580 | A1 | 9/2005 | Prentice et al. |
| 2006/0136001 | A1 | 6/2006 | Ortega et al. |
| 2006/0224224 | A1 | 10/2006 | Muhlenberg et al. |
| 2007/0060961 | A1 | 3/2007 | Echt et al. |
| 2007/0129764 | A1 | 6/2007 | Burnes |

OTHER PUBLICATIONS

Product Brochure, "ATROSTIM Phrenic Nerve Stimulator," AtroTech Oy, P.O. Box 28, FIN-33721 Tampere, Finland, 2 pages (Jun. 2004).

Ravazzi, et al., "Improvement of Interventricular Activation Time Using Biphasic Pacing Pulses at Different Sites on Right Ventricle Septal Wall," *Progress in Biomedical Research*, pp. 248-253 (Jun. 1999).

Saksena, et al., "Electrical Therapy for Cardiac Arrhythmias," Chapter 9, "Pacemaker Implantation Techniques," pp. 173, 181-183, W.B. Saunders Co., Philadelphia, PA, USA (1990).

(Exh. A), *Effects of Right Ventricular Pacing on Intra-Left Ventricular Electromechanical Activation in Patients With Native Narrow QRS*, by Gabriele Lupi et al., *American Journal of Cardiology*, 2006;98:219-222.

(Exh. B), *Heart Failure During Cardiac Pacing*, by Michael O. Sweeney et al., *Circulation*, 2006;113:2082-2088.

(Exh. C), *Adverse Effect of Ventricular Pacing on Heart Failure and Atrial Fibrillation Among Patients With Normal Baseline QRS Duration in a Clinical Trial of Pacemaker Therapy for Sinus Node Dysfunction*, by Michael O. Sweeney et al., *Circulation*, 2003;107:2932-2937.

1997 (Exh. D), *Longitudinal Dissociation In The His Bundle. Bundle Branch Block Due To Asynchronous Conduction Within The His Bundle In Man*, by Onkar S. Narula, M.D., Circulation, vol. 56, No. 6, Dec. 1977.

(Exh. D1), *Narrowing and normalization of QRS by stimulation of the His bundle in complete left bundle branch block*, by P. Puech et al., Scholarly Journal of the French Cardiology Society, vol. 72, No. 8, Aug. 1979. English translation thereof, followed by French publication.

(Exh. D2), *Bundle Branch Blocks Anatomically Located In The His Bundle*, by P. Alboni, Italian Cardiology Journal, vol. 10, No. 12, 1980. English translation thereof, followed by Italian publication.

(Exh. E), *Biventricular Pacing Worsened Dyssynchrony In Heart Failure Patient With Right-Bundle Branch Block*, by Masaki Tanabe et al., Int'l Journal of Cardiology, in press 2008 (doi:10.1016/j.ijcard.2008.06.063).

* cited by examiner

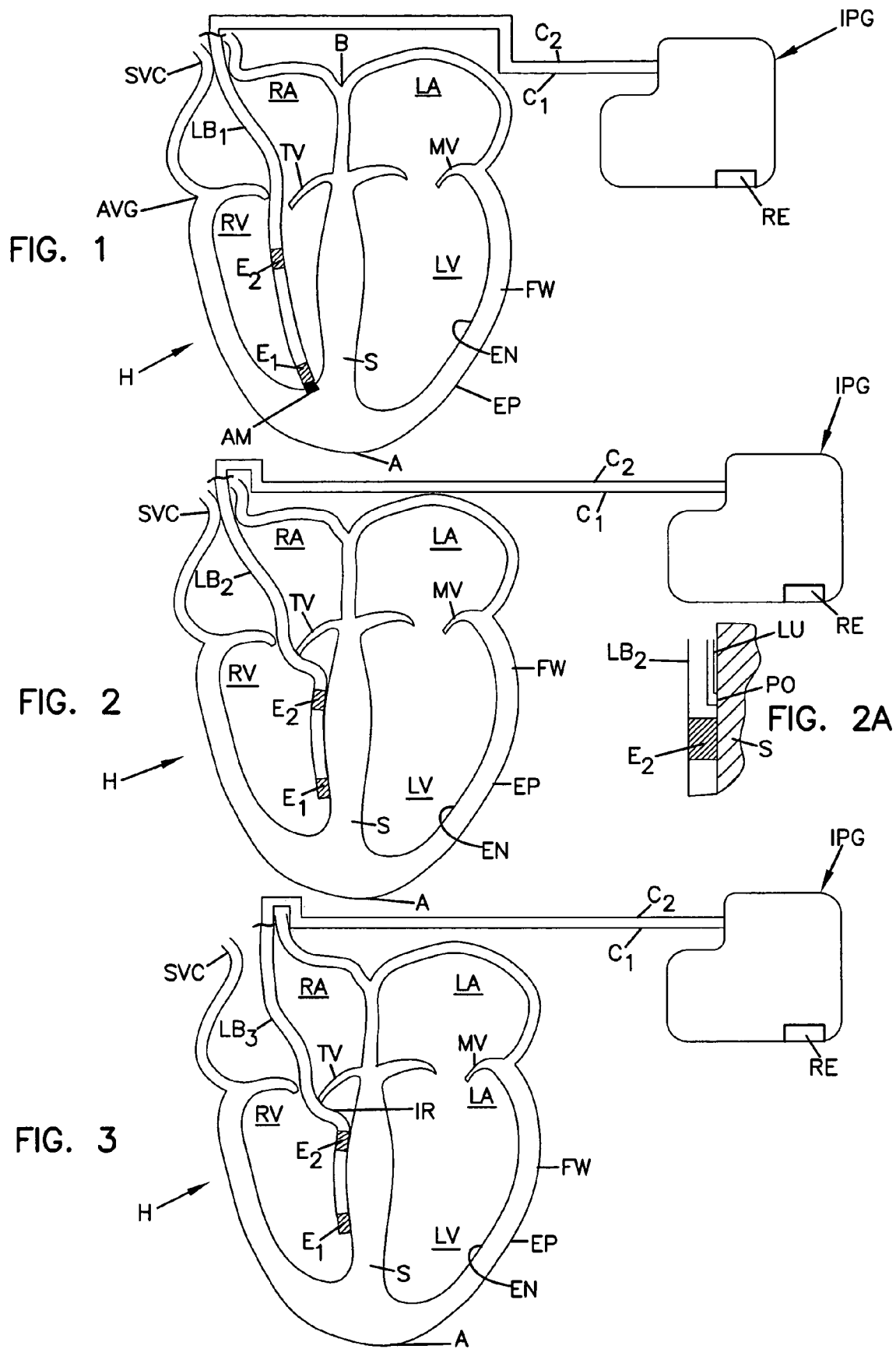

FIG. 18A
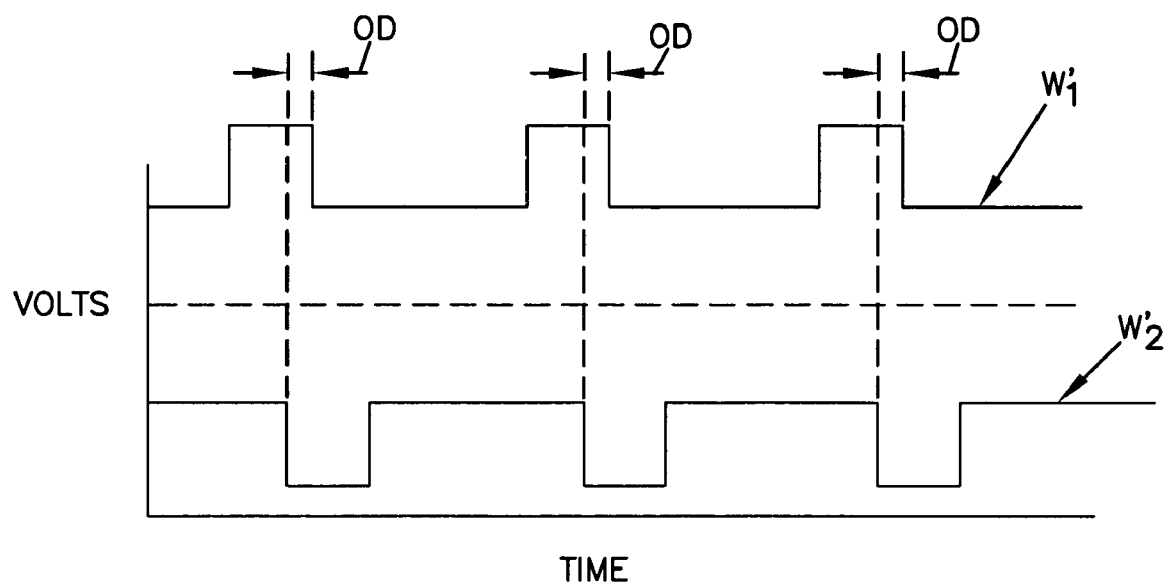
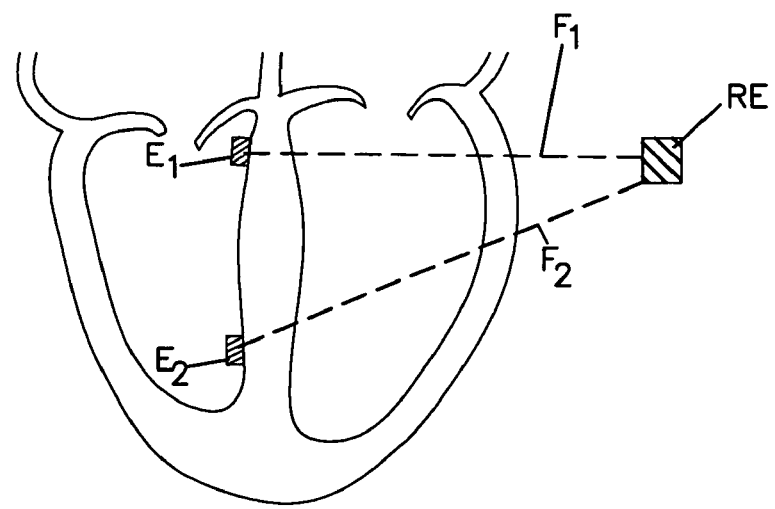
FIG. 18B

VENTRICULAR PACING

I. CROSS REFERENCE TO RELATED APPLICATION

The present application claims priority to Argentine Patent Application Ser. No. P 040104782 filed Dec. 20, 2004 filed by inventors Daniel Felipe Ortega and Alberto German Giniger and entitled "A NEW PACEMAKER WHICH REESTABLISHES OR KEEPS THE PHYSIOLOGICAL ELECTRIC CONDUCTION OF THE HEART AND A METHOD OF APPLICATION".

II. BACKGROUND OF THE INVENTION

1. Field of the Invention

This invention pertains to ventricular pacing. More particularly, this invention pertains to synchronous pacing of a patient's left ventricle by electrodes residing in the patient's right ventricle.

2. Description of the Prior Art a. Pacing for Bradycardia

Percutaneously placed pacing electrodes are commonly positioned only in the right-side chambers (right atrium or right ventricle) of the heart. Access to such chambers is readily available. Such access is through the superior vena cavity into the right atrium and then into the right ventricle.

Electrode placement into the left ventricle is normally avoided. Access is not as direct as in right ventricle placement. More important, emboli risk in the left ventricle is greater than in the right ventricle. Emboli which might develop in the left ventricle by reason of the electrode placement have direct access to the brain via the aorta from the left ventricle. This presents a significant risk of stroke.

Historically, pacing electrodes were placed only in the right ventricle to treat bradycardia (slow heart rate). Right atrium pacing was less understood and was more complex.

With advances in electro-physiology, pacing of both the right atrium and right ventricle was developed. Such dual chamber pacing resulted in better hemodynamic output than right ventricle-only pacing.

In addition to treating bradycardia, dual chamber pacing maintained synchrony between the chambers. Recent clinical evidence suggests that conventional ventricular pacing from the right ventricle creates asynchronous contraction of the left ventricle, leading to inefficient mechanical contraction and reduced hemodynamic performance. Long term right ventricular pacing has even been found to be associated with an increased risk of developing or worsening heart failure.

At first, combined pacing of the right ventricle and right atrium was performed by advancing two electrode leads through the superior vena cava into the right atrium. The first of these terminated at one or more electrodes which were attached to the endocardium of the atrium. The second lead (also having one or more electrodes) was advanced into the right ventricle with the electrode attached to the endocardium of the right ventricle.

Such historical dual chamber pacing was not without complications. The use of two leads resulting in a doubling of volume of the vasculature (e.g., the superior vena cava and jugular vein) occupied by such leads. Further, attachment of an electrode to the atrial wall was unreliable.

The historical problems of the dual chamber pacing led to the development of so-called "single pass" leads. Such leads have both the atrial and ventricle electrodes on a common lead.

An example of a single pass lead for pacing both the right ventricle and right atrial is taught in U.S. Pat. No. 6,230,061 B1 to Hartung issued May 8, 2001. The lead of the '061 patent is described as floating lead in that the lead and electrodes are not attached to the walls of the heart. In one embodiment of the '061 patent (FIG. 4a), two electrodes in the right atrium pace the right atrium. In a second embodiment (FIG. 4b), an electrode resides in the right ventricle to add right ventricular pacing. As will be described, the '061 patent describes an oppositely polarized electrode (which may be exposed on a subcutaneously placed implantable pulse generator).

It is Applicants' understanding the design of the '061 patent has not enjoyed great commercial success. Applicants believe this is due, at least in part, to the separate development of smaller profile leads and more reliable atrial attachment techniques. Both of these developments address the problems of dual chamber pacing otherwise addressed by the '061 patent.

b. Pacing for Congestive Heart Failure

Beginning in the 1990's, cardiac pacing has been considered for treatment of congestive heart failure (CHF). CHF patients suffer from low left ventricular output.

CHF is an extremely serious and progressive disease. While drug treatments exist, they may delay but do not stop or reverse the disease.

CHF patients face a progression of a debilitating condition which drastically alters lifestyle and will ultimately be fatal in the absence of heart transplant. Unfortunately, many patients do not qualify for such transplants and the available number of donor hearts is inadequate to treat those who do qualify.

Many CHF patients have low left ventricular output due to a mismatch between contractile forces produced by muscles of the left ventricle free wall (the external wall of the left ventricle) and the opposing septum (the wall dividing the right and left ventricles). Ideally, the free wall and septum contract in synchrony during systole to urge blood through the aortic valve. When out of synchrony, the septal wall may be contracting while the free wall is relaxed. Instead of urging blood flow, at least a portion of the contractile energy of the septum is wasted.

The mismatch of free wall and septal contractility is believed to be due to disorders in the electrical conduction systems of the heart. This conduction system includes the A-V node, the Bundle of His and the Purkinje fibers.

Located at the upper end of the septum, the sinus node creates the synchronized neuraly-mediated signal for cardiac pacing. These signals are conducted by the specialized fibers comprising the A-V node and the Bundle of His (extending along the length of the septum) and further conducted to the muscle of the heart through the Purkinje fibers. The Purkinje fibers originate in the septum and extend through the apex of the heart and to the exterior walls of the heart including into and up the free wall of the left ventricle.

In a healthy heart, the signal flow from the A-V node to the free wall of the left ventricle is rapid to insure the free wall and septum contract in synchrony. For example, a stimulating signal may flow to the free wall in about 70-90 milli-seconds. In patients with conduction abnormalities, this timing may be significantly delayed (to 150 milli-seconds or more) resulting in asynchronous contraction.

In some patients, the conduction path through the Purkinje fibers may be blocked. The location of the block may be highly localized (as in the case of so-called "left bundle branch block" or LBBB) or may include an enlarged area of dysfunctional tissue (which can result from infarction). In such cases, all or a portion of the free wall of the left ventricle is flaccid while the septum is contracting. In addition to contributing to asynchronous contraction, the contraction force of the free wall is weakened.

To address asynchronous contraction, CHF patients can be treated with cardiac pacing of the left ventricle. Such pacing includes applying a stimulus to the septal muscles in synchrony with stimulation applied to the muscles of the free wall of the left ventricle. While infracted tissue will not respond to such stimulus, non-infarcted tissue will contract thereby heightening the output of the left ventricle.

The prior art has developed various techniques for accomplishing left ventricle stimulation. For reasons noted above (i.e., emboli formation), endocardially positioned electrodes in the left ventricle are avoided. However, electrodes can be placed on the epicardial surface of the heart through surgical placement. The epicardial electrodes are positioned on the free wall of the left ventricle and are paced in synchrony with electrodes placed near the septum in the right ventricle.

Since epicardial electrodes require a surgical placement, the patient is subjected to two procedures—percutaneous placement of right ventricle electrodes (normally performed in a catheter lab by an electrophysiologist) and surgical placement of epicardial electrodes on the left ventricle (normally placed by a cardiac surgeon in a surgical suite). Also, such dual procedure is a burden on medical resources.

Percutaneous procedures have been developed for placement of an electrode to stimulate the free wall of the left ventricle. In such a procedure, an electrode lead is advanced through the coronary sinus. Part of the venous system, the coronary sinus extends from the right atrium and wraps around the heart on or near the epicardial surface and partially overlies the left ventricle free wall. In this percutaneous procedure, the electrode remains positioned in the coronary sinus overlying the left ventricle free wall with the lead passing through the coronary sinus and through the right atrium to the implantable pulse generator.

Unfortunately, a coronary sinus electrode is frequently less than optimal. The portion of the free wall most directly influenced by the electrode is the tissue directly underlying the coronary sinus at the location of the electrode. For many patients, this may not be the location of the free wall most in need of a stimulating therapy. Accordingly, the resulting therapy is sub-optimal. Also, some patients may have an extremely small diameter coronary sinus or the coronary sinus may have such a tortuous shape that percutaneous positioning of an electrode within the coronary sinus is impossible or very difficult. Not uncommonly, advancing a lead from the right atrium into the coronary sinus is extremely time-consuming. Even if successful, such a procedure consumes significant health care resources (including precious catheter lab time). Finally, there are now up to three leads passing through and occupying the space of the superior vena cava (i.e., leads for the electrodes in the right ventricle, right atrium and the coronary sinus). U.S. patent application Publ. No. 2005/0125041 published Jun. 9, 2005 shows (in FIG. 1) three leads passed through a superior vena cava with one lead residing in the right atrium, one in the right ventricle and one passed through the coronary sinus to overly the left ventricle.

Attempts at pacing the left ventricle by pacing stimulation in the right ventricle have been suggested. U.S. Pat. No. 6,643,546 B2 to Mathis et al. dated Nov. 4, 2003 describes a lead with an array of electrodes along its length. The lead is placed in the right atrium and extending through the right ventricle, along the septal wall, and into the pulmonary artery. The concept requires that multiple electrodes from the array be pulsed simultaneously at significantly high voltages to produce an adequate electrical field to stimulate the LV septum. The current output from the pulse generator and battery will be very high due to the multiplicity of electrodes and high pacing voltages. Such high output will cause a clinically unacceptable product lifespan. Since a large number of electrodes and supporting electronics are needed to implement such a therapy delivery mechanism, it is not known yet whether it is practically feasible, not least to mention that it is very complicated both in terms of device design/manufacturing as well clinical practice. No published reports known to this date have demonstrated the functional as well as clinical benefits for this multiple electrode stimulation approach in the ventricle.

As will be described with reference to a preferred embodiment, the present invention is directed to a left ventricle pacing system and method which does not require epicardial electrodes or electrodes in a coronary sinus. As will be described, the present invention includes electrodes in the right ventricle near the septal wall. These electrodes create a pulsed electrical field which stimulates both the septum and at least a portion of the free wall of the left ventricle. The present invention achieves these objectives without requiring excessive energy demands or power consumption.

III. SUMMARY OF THE INVENTION

According to a preferred embodiment of the present invention, a method and apparatus are disclosed for treating a condition of a patient's heart. The method includes placing a first electrode and a second electrode in a right ventricle of the heart. A reference electrode is placed within the patient and internal or external to the heart. A pacing signal is generated including a first signal component, a second signal component and a reference component with the first and second signal components having opposite polarity and with both of the first and second components having a potential relative to the reference component. The first component is transmitted to the first electrode. The second component is transmitted to the second electrode. The reference electrode is connected to the reference component which may be an electrical ground. The pacing signal and the placement of the electrodes are selected to alter a contraction of a left ventricle of the heart.

IV. BRIEF DRESCRIPTION OF THE DRAWINGS

FIG. 1 is a schematic cross sectional view of the heart showing relevant anatomical features and schematically showing a catheter with pacing electrodes in the right ventricle and a subcutaneously placed implantable pulse generator;

FIG. 2 is the view of FIG. 1 showing electrodes in contact with a septal wall;

FIG. 2A is a cross-sectional view of an electrode lead showing a mechanism for attachment of an electrode to a septal wall;

FIG. 3 is the view of FIG. 1 showing an electrode lead formed, in part, from shape memory alloys for urging electrodes against a septal wall;

FIG. 18A is a view similar to that of FIG. 18 showing alternative waveforms;

FIG. 18B is a view similar to FIG. 18 and showing two electrodes creating two separate fields to a reference electrode;

V. DESCRIPTION OF A PREFERRED EMBODIMENT

Figure 4:
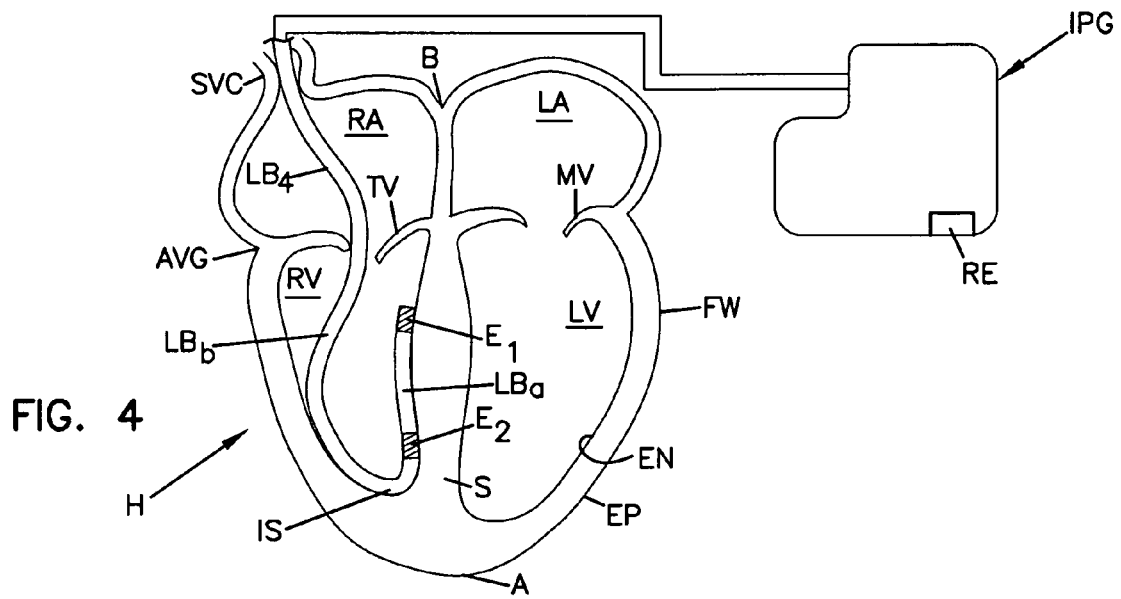
FIG. 4 is the view of FIG. 1 showing a further embodiment of an electrode lead for urging electrodes against a septal wall.

Referring now to the various drawing figures, a description of the preferred embodiment of the present invention will now be provided. Incorporated herein by reference are the disclosures of U.S. Pat. No. 6,230,061 B1 to Hartung issued May 8, 2001 and U.S. Pat. No. 6,907,285 to Denker, et al., dated Jun. 14, 2004; U.S. patent application Publ. No. 2004/0153127 published Aug. 5, 2004; U.S. Pat. No. 6,643,546 B2 to Mathis et al. dated Nov. 4, 2003.

A. Placement of an Electrode Pair in the Right Ventricle

Generally speaking, the present invention is directed to creating a pulsed electrical field in the right ventricle with the field stimulating the musculature of the septum and free wall of the left ventricle to create coordinated contraction of the septum and free wall.

The present invention can be practiced with currently commercially available electrode leads and can also be enhanced with novel leads. FIG. 1 illustrates the invention in practice with such commercially available lead. As is the conventional usage for referencing relative direction, the terms "left" and "right" are used herein with reference to the patient's perspective. The terms "upper" and "lower" and similar terms such as "up" or "down" are used with reference to the base B of the heart being high and the apex A of the heart H being a lower end.

In FIG. 1, a patient's heart H is schematically shown in cross-section. The heart H includes the upper chambers of the right atrium RA and left atrium LA. The lower chambers are the right ventricle RV and left ventricle LV. Of the various venous vessels opening into the right atrium RA, only the superior vena cava SVC is shown. Also, of the various heart valves, only the mitral valve MV (separating the left atrium LA from the left ventricle LV) and the tricuspid valve TV (separating the right atrium RA from the right ventricle RV) are shown. The septum S separates the right and left ventricles RV, LV and the free wall FW of the left ventricle LV is separately labeled. The surface of the heart wall tissue opposing the chambers is the endocardium and is labeled as EN. The exterior surface of the heart is the epicardium and is labeled EP. Not shown are coronary vessels of the heart or the pericardium surrounding the heart H.

In FIG. 1, an electrode lead is shown having a lead body $LB_1$ and exposed electrodes $E_1$ and $E_2$. The first electrode $E_1$ is positioned near the distal tip of the lead body $LB_1$. The second electrode $E_2$ is positioned more proximally on the lead body $LB_1$. At the distal end, an attachment mechanism AM (such as a passive fixation design with tines or an active fixation design with a metallic helix) is shown for securing the first electrode $E_1$ to the musculature of the heart H. The spacing of electrodes $E_1$, $E_2$ could be greater than that of convention pacing electrodes permitting positioning of the first electrode $E_1$ at the apex of the right ventricle RV and the second electrode $E_2$ in the right ventricle RV near the tricuspid valve TV. However, conventional leads with convention spacing have been used with the first or distal electrode attached to the septum (e.g., by a helix attachment HA) as shown in FIG. 7A.

The lead body $LB_1$ is flexible and includes a bio-compatible, electrically insulating coating surrounding first and second conductors $C_1$, $C_2$ separately connected to the first and second electrodes $E_1$, $E_2$. In the various Figures, the lead bodies are broken at a line at the SVC to reveal the internal conductors $C_1$, $C_2$ extending to an implantable pulse generator IPG. In fact, the conductors $C_1$, $C_2$ are contained within the material of the lead body $LB_1$ along their length. The term "implantable pulse generator IPG" is intended to include pacemakers, implantable converter defibrillators (ICD) and cardia resynchronization therapies (CRT), all known in the art.

The proximal end of the lead body terminates at a pin connector (not shown) as is customary. The pin connector has exposed electrical contacts uniquely connected to each of the conductors $C_1$, $C_2$. The pin connector may be releasably connected to the pulse generator IPG with the exposed contacts making electrical connection with unique contacts of the circuitry of the pulse generator IPG.

It will be appreciated that the prior art contains numerous examples of cardiac leads for placement in a chamber of the heart where the leads have, as described above, two or more electrodes spaced along a length of the lead, attachment mechanisms such as passive or active fixation and conductors and connector pins as described. The current invention is not limited to pacing leads only, but rather is equally deployable with prior art ICD leads where it is customary to contain at least two electrodes in the RV. Such leads are selected of biocompatible material and treated (such as sterilized) for chronic placement in the patient.

The implantable pulse generator IPG is a small metallic container sealed for implantation in the patient and protecting internal circuitry. Commonly, such pulse generators are placed subcutaneously (e.g., in a dissected space between the skin and muscle layers of the patient). For cardiac pacing, such pulse generators are positioned in the upper chest on either the left or right front side of the patient near a shoulder. However, placement need not be so restricted and such pulse generators could be placed in any convenient location selected by the physician.

Pulse generators contain internal circuitry for creating electrical impulses which are applied to the electrodes after the lead is connected to the pulse generator. Also, such circuitry may include sensing and amplification circuitry so that electrodes $E_1$, $E_2$ may be used as sensing electrodes to sense and have the IPG report on the patient's electrophysiology.

The lead may be introduced to the vasculature through a small incision and advanced through the vasculature and into the right atrium RA and right ventricle to the position shown in FIG. 1. Such advancement typically occurs in an electrophysiology lab where the advancement of the lead can be visualized through fluoroscopy.

The pulse generator contains a battery as a power supply. With subcutaneous placement, replacement of a battery is well-known procedure. However, improvements in battery designs have resulted in longer-lasting batteries with the benefit of reducing the frequency of battery replacement. Alternatively, such batteries may be rechargeable in situ as is known in the art.

The pulse generator circuitry controls the parameters of the signals coupled to the electrodes $E_1$, $E_2$. These parameters can include pulse amplitude, timing, pulse duration by way of example. The internal circuitry further includes circuit logic permitting reprogramming of the pulse generator to permit a physician to alter pacing parameters to suit the need of a particular patient. Such programming can be affected by inputting programming instructions to the pulse generator via wireless transmission from an external programmer. Pulse generators commonly include an exposed contact on the exterior of the generator housing. Such pulse generators may also be partially covered with an insulator such as silicone with a window formed in the silicone to expose a portion of the metallic housing which functions as a return electrode in so-called unipolar pacing. In conventional bipolar pacing, the window is not necessary. Most commonly, the electrode is connected by the circuitry of the housing to an electrical ground. It will be appreciated that pulse generators as thus described are well known in the art and form no part of this invention per se.

While an implantable pulse generator is described in a preferred embodiment, the pulse generator may be external and coupled to the electrodes by percutaneous leads or wireless transmission. For example, a control of an implanted electrode is known for phrenic nerve stimulation and is described more fully in a product brochure "ATROSTIM PHRENIC NERVE STIMULATOR", AtroTech Oy, P.O. Box 28, FIN-33721, Tampere, Finland (June 2004). The Atrostim device sends signals from an external controller to an implanted antenna.

External pacing devices are typically used for providing temporary pacing therapy. The current invention is also believed to have advantages for this application as critically-ill patients requiring emergency, temporary pacing may also suffer further from asynchronous cardiac contraction associated with conventional RV pacing. If desired, an external unit can be used to test a patient's suitability for the treatment. Patient's who benefit from the therapy can then receive an implantable pulse generator for longer-term use.

Figure 8:
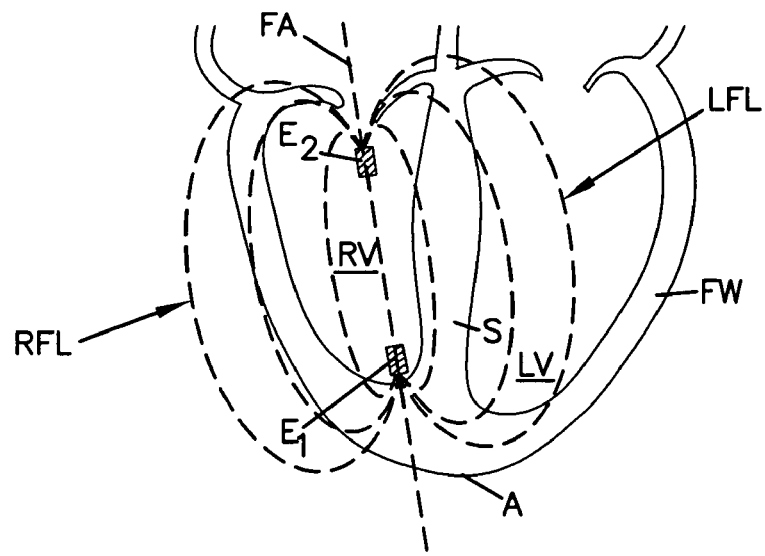
FIG. 8 is a view, taken in cross-section, of right and left ventricles of a heart showing the electrodes of FIG. 1 (without showing the lead body) energized to create electromagnetic fields.

B. Right Ventricle Electrodes Creating Left Ventricle-Stimulating Electrical Field FIGS. 1 and 8 illustrate commercially available leads and the associated electrical fields with both electrodes residing within the right ventricle with the distal electrode secured to the apex of the right ventricle. In FIG. 8, only the ventricles RV, LV are shown for ease of illustration. Also, for ease of illustration, FIG. 8 shows only the electrodes $E_1$, $E_2$ without showing the remainder of the lead body $LB_1$.

While conventional bipolar leads are acceptable for use with the present invention, a wider spacing between electrodes $E_1$, $E_2$ can increase the field but can sacrifice some sensing capability. This trade-off can be mitigated by use of a three-electrode lead in the right ventricle RV. Such a lead would have a tip electrode and two ring electrodes, one located near the tip in the RV apex and one in the high part of the atrium, near the tricuspid valve. The sensing is performed between the tip and closer electrode. This will provide good so-called "near field" sensing and avoid so-called "far field" sensing of the atrium or skeletal muscle activity. The pacing could be between the ring electrodes to the return electrode located distally to the heart (as will be described). One could also combine the tip and nearest ring as one electrode to the return electrode and the other ring electrode to the return electrode at the opposite polarity.

Figure 18:
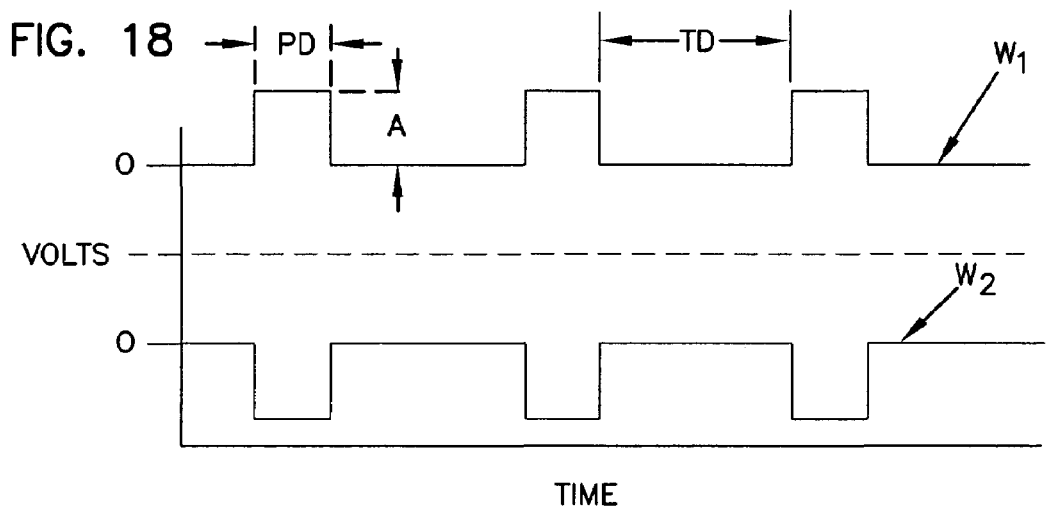
FIG. 18 is a graphical representation of pulsed waveforms to be applied by first and second electrodes of the various embodiments.

The pulse generator IPG generates a first and a second pulsed waveform $W_1$, $W_2$ applied, respectively, to the first and second electrodes $E_1$, $E_2$. FIG. 18 shows such waveforms $W_1$, $W_2$. By way of example, and not intended to be limiting, the pulse duration PD is between about 0.1 to 2.0 milliseconds, the amplitude A may be 0.1 Volts to 10 or 20 Volts and the time delay TD between pulses is a targeting heart rate (e.g., 50 to 200 beats per minutes).

In FIG. 18, the pulses are shown as square waveforms but, in practice, can be any geometry. The first electrode $E_1$ has positive charged pulses only. The second electrode $E_2$ has negative charged pulses timed to coincide with the positive charged pulses of the positive electrode $E_1$. While direct current (DC) pulses are preferred, the electrodes $E_1$, $E_2$ could be energized with alternating current pulses with the signals to the electrodes $E_1$, $E_2$ out of phase such that the positive pulses on the first electrode $E_1$ coincide with negative pulses on the second electrode $E_2$ and negative pulses on the first electrode $E_1$ coincide with positive pulses on the second electrode $E_2$.

With the electrodes $E_1$, $E_2$ charged with opposite pulses, it is Applicants' current understanding that an electrical field is created between the electrodes $E_1$, $E_2$ with a field axis FA (FIG. 8) extending in a line between the electrodes $E_1$, $E_2$. In the absence of distorting influences (such as external magnetic fields, external electrodes or non-homogonous conductivity due to variances in conductivity of blood, tissue bone, etc.), the field is symmetrical about the field axis FA and is represented by field lines illustrated in the drawings as left field lines LFL to the left of the axis FA (with left being from the patient's perspective) and right field lines RFL. The field lines represent the intensity of the electrical field. The intensity diminishes rapidly as a function of the distance from the field axis FA.

In the embodiment of FIG. 1, in order for the fields generated by the electrodes $E_1$, $E_2$ to have a significant influence on both the septal walls and the free wall FW of the left ventricle LV, a voltage potential across the electrodes must be substantially high. However, such high voltages are not practical in a pacing electrode and are more normally associated with defibrillating treatments. Also, such voltages would cause an extremely significant drain on a battery requiring an impractical frequency of battery replacement.

C. Improving Field Influence on Left Ventricle

Figure 9:
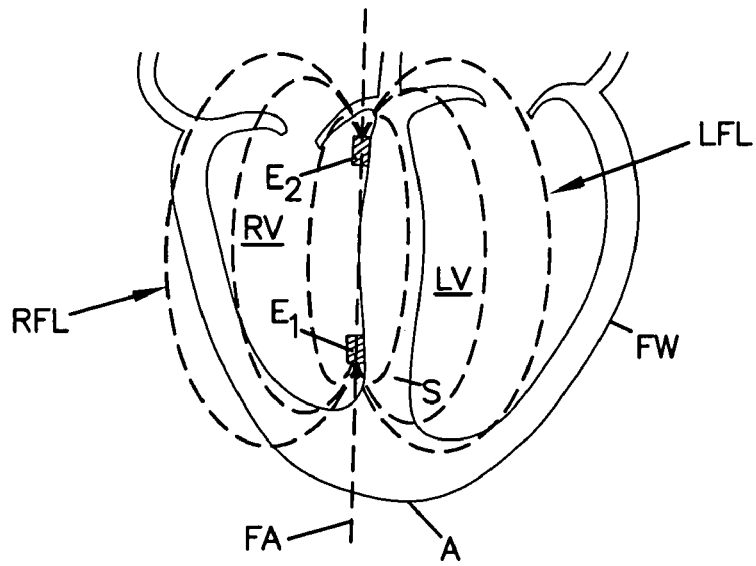
FIG. 9 is the view of FIG. 8 showing the field shifted toward the left ventricle in response to repositioning of leads.

FIG. 9 illustrates benefits associated with movement of the electrodes $E_1$, $E_2$ from the interior of the right ventricle RV (FIGS. 1 and 8) to direct placement of the electrodes $E_1$, $E_2$ on the septal wall S. Such movement shifts the field lines toward both the septal wall S and the free wall FW of the left ventricle LV. However, it is believed that even with such improvement, voltages required for effective stimulation of the septal wall and the free wall of the left ventricle would be impractically high.

Figure 10:
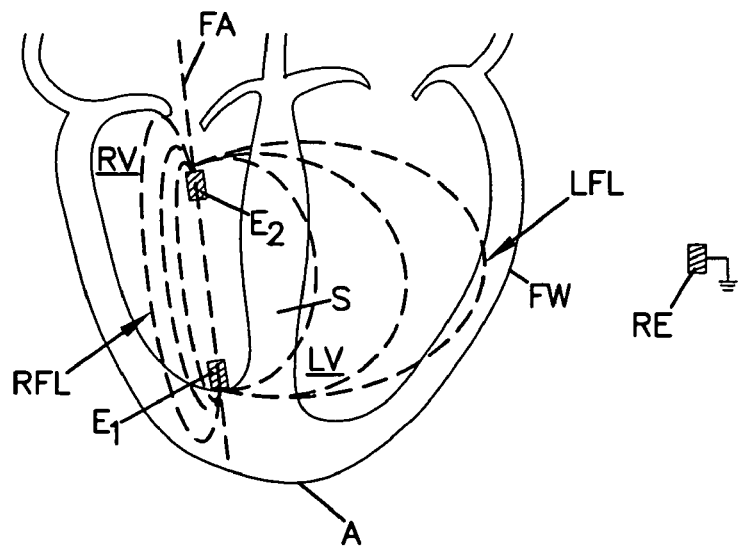
FIG. 10 is the view of FIG. 8 showing the field distorted toward a free wall of the left ventricle by influence of an external reference electrode.

The present invention utilizes a reference electrode RE in combination with the electrodes $E_1$, $E_2$ in the right ventricle to result in effective pacing of the left ventricle LV. Although the physics and physiology of the mechanism of action are not fully understood, it is presently believed that the reference electrode RE distorts the electromagnetic field otherwise created between the right ventricle electrodes $E_1$, $E_2$ to urge an intensity of the electromagnetic field deeper into the septal wall S of the left ventricle LV. It is believed this occurs by creating a third high current density spot (or spots) away from the two electrodes in the wall and towards the reference electrode at the point where the current flows between the electrode E1 and the reference electrode RE and between the electrode E2 and the reference electrode RE coincide in space and time. This is illustrated in FIG. 10. Such a phenomenon is believed to facilitate the activation of the surviving conduction fibers in the Left Bundle Branch Block (LBBB) patients and Purkinje fibers and create a more rapid and uniform activation of the left ventricle LV that follows a similar pattern to the normal activation present in patients without LBBB.

The reference electrode may be physically attached to the housing of the implantable pulse generator IPG (and thereby having a neutral charge). Such an electrode RE is shown in FIGS. 1-7B. It will be appreciated that the reference electrode RE can be connected to the implantable pulse generator IPG by a conductor. The reference electrode could be another common electrode that exists in the conventional pacing or ICD system, such as an electrode in the atrium or a defibrillation coil electrode situated in the SVC, RA or RV.

As shown in FIG. 10, the consequence of the reference electrode RE is presently believed to have a deforming effect on the electromagnetic field generated between the first and second electrodes $E_1$, $E_2$. This is illustrated in FIG. 10 by distorting the left field lines LFL toward the septal wall S and free wall FW of the left ventricle LV. Also, the right field lined RFL are compressed toward the axis FA to alter the field from the symmetric presentation of FIGS. 8 and 9 to the asymmetric presentation of FIG. 10 with the field biased toward the septal wall S and the free wall FW of the left ventricle LV.

It has been found that within energy levels associated with available implantable pulse generators (up to 10 or 20 volts) effective activation of the left ventricle LV can be achieved with the pacing arrangement of FIG. 7A, where the first electrode $E_1$ is attached to the mid- or upper-septum. In such arrangement, the reference electrode RE is on the housing of the generator IPG and positioned subcutaneously near the right or left shoulder. The re-direction of the field as described, the inventors believe, may also be useful in decreasing defibrillation thresholds if arrangement similar to FIG. 7B is used. In FIG. 7B large segmented (for flexibility) electrodes E2, E3 are shown in the superior vena cava SVC near the atrium RA and in the right ventricle to serve as shocking electrodes to defibrillate a patient.

D. Various Alternative Embodiments

Figure 14:
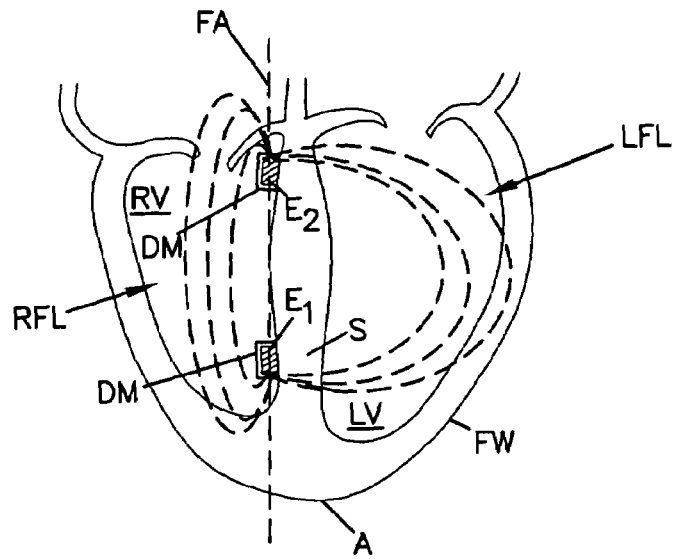
FIG. 14 is the view of FIG. 9 with fields distorted to be biased toward the left ventricle by the addition of dielectric material on a side of the electrodes of FIG. 9.

FIG. 14 illustrates how the field can also be distorted by dielectric material DM placed on a side of the electrodes $E_1$, $E_2$ opposite the septal wall S. The dielectric material DM result in a distortion of the electrical field biasing the left field lines LFL toward the septal wall S and the free wall FW. Of course, this configuration will work even better with a reference electrode which will enhance the benefit.

While positioning of the electrodes $E_1$, $E_2$ within the volume of the right ventricle RV is effective in combination with a reference electrode RE (FIG. 10), movement of the electrodes $E_1$, $E_2$ directly against the septal wall S may further enhance the therapeutic benefit of the present invention for reasons described above. Various techniques for movement of the electrodes $E_1$, $E_2$ against the septal wall S are disclosed.

FIG. 2 illustrates a lead body $LB_2$ in the right ventricle RV with the electrodes $E_1$, $E_2$ directly placed on the septal wall S and held in place against the septal wall through any suitable means. For example, FIG. 2A illustrates one embodiment for attachment of an electrode against the septal wall. The lead body $LB_2$ is shown has having an internal lumen LU with a port PO near an electrode (e.g., electrode $E_2$). Any suitable attachment mechanism (such as a pigtail guidewire or an injected bio-adhesive) can be passed through the lumen LU and port PO to fix the electrode $E_2$ in abutment against the septal wall S. Further, a guide catheter could also be used in moving the implantable lead to assist in the mapping of the optimal location of the septum. The optimal lead location can be determined with the assistance of the surface ECG parameters (e.g. QRS width and/or activation vectors).

FIG. 3 illustrates the electrodes $E_1$, $E_2$ against the septal wall S but without requiring an attachment mechanism. Instead, an intermediate region IR of the lead body $LB_3$ is formed of shaped memory material (such as nitinol) to assume an S-shaped configuration and urge the electrodes $E_1$, $E_2$ against the septal wall S.

In FIG. 4, the lead body $LB_4$ has two components $LB_a$, $LB_b$ joined by an intermediate section IS which may be formed of any elastomeric material (such as a shaped memory material). The intermediate section IS is biased to urge the two components $LB_a$, $LB_b$ into collinear alignment. With the intermediate section IS placed against the apex of the right ventricle RV, the bias of the intermediate section IS urges the electrodes $E_1$, $E_2$ against the septal wall S.

Figure 5:
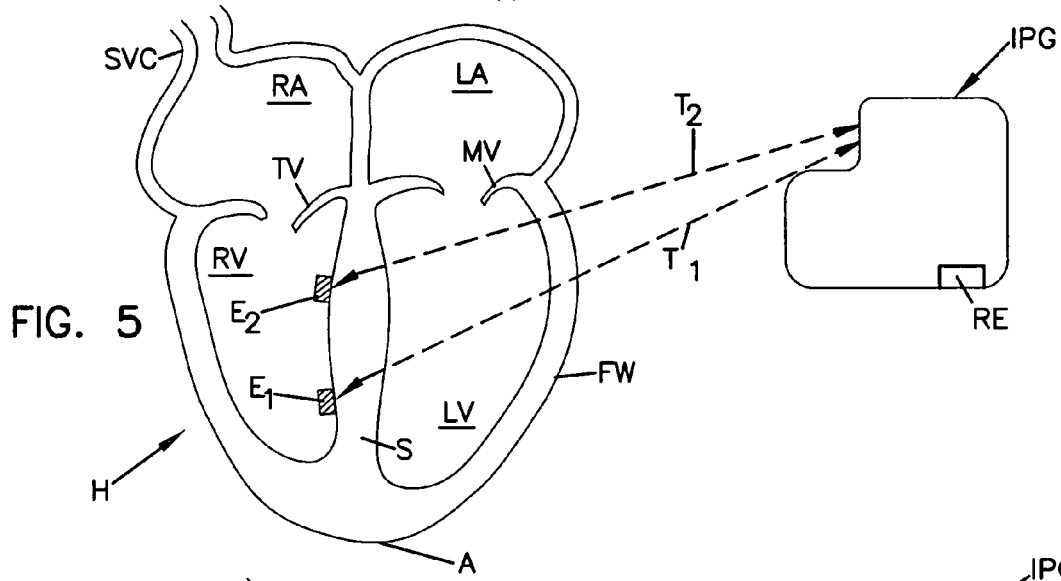
FIG. 5 is the view of FIG. 1 showing electrodes on a septal wall and energized by wireless transmission.
Figure 6:
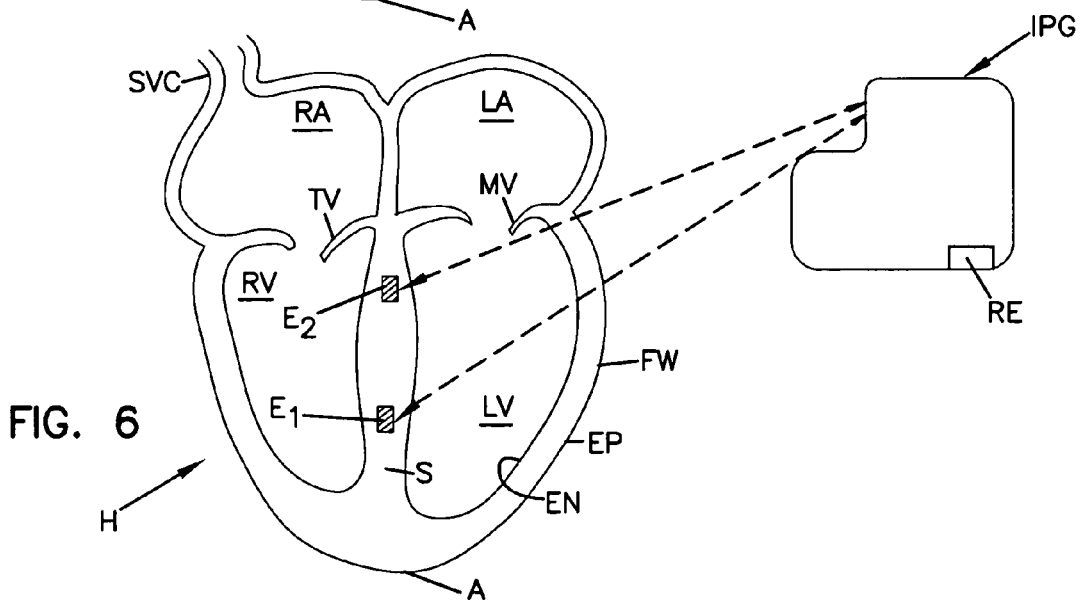
FIG. 6 is the view of FIG. 5 showing electrodes embedded within the septal wall.

FIG. 5 illustrates the electrodes $E_1$, $E_2$ individually placed on the septal wall S and not retained on a lead body. In such an embodiment, the electrodes $E_1$, $E_2$ may be energized in a pacing waveform by wireless transmission signals $T_1$, $T_2$ from the implantable pulse generator IPG. Wireless transmission from a controller to an electrode is shown in U.S. Pat. No. 6,907,285 to Denker, et al., dated Jun. 14, 2004. Alternatively, the electrodes $E_1$, $E_2$ may be directly imbedded as microstimulators into the tissue of the septal wall S as illustrated in FIG. 6. Microstimulators for implantation into human tissue are shown in U.S. patent application Publ. No. 2004/0153127 published Aug. 5, 2004.

Figure 11:
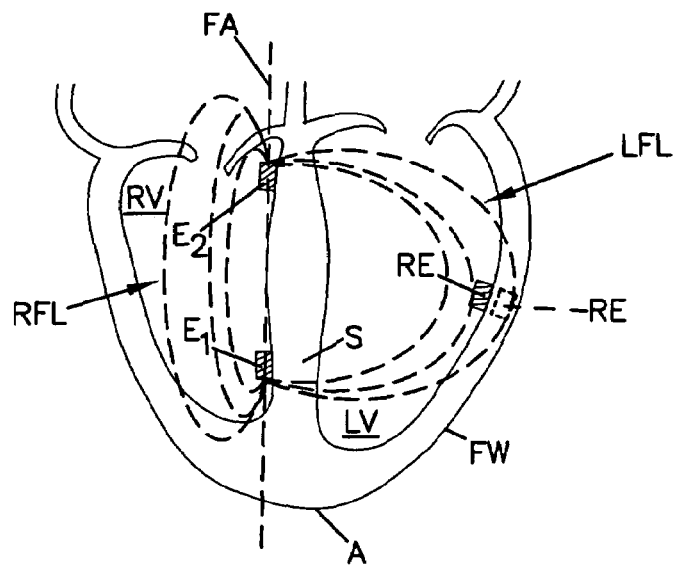
FIG. 11 is the view of FIG. 9 with a reference electrode placed within the left ventricle.
Figure 12:
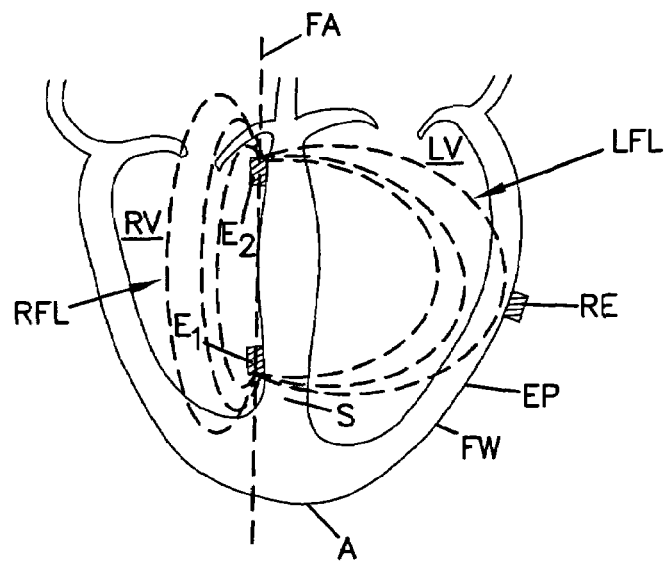
FIG. 12 is the view of FIG. 14 with an external electrode placed on the epicardial surface of the heart.
Figure 13:
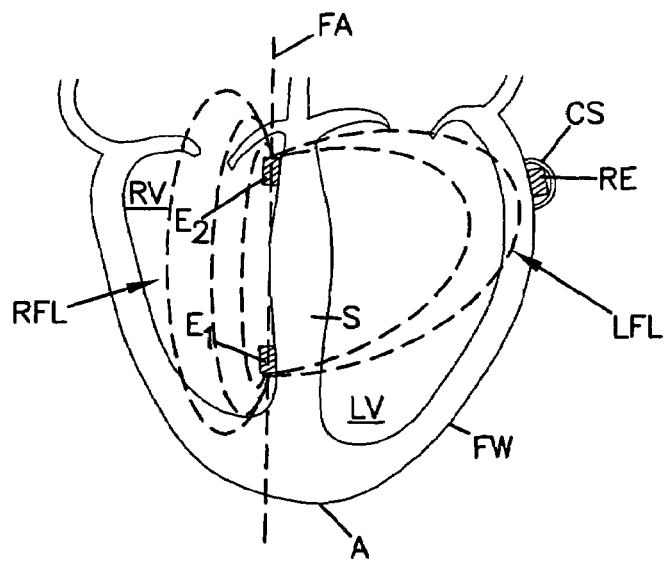
FIG. 13 is a view with an external electrode placed within a coronary sinus.

The positioning of the reference electrode RE may be directly on the housing of the implantable pulse generator IPG or may be separate from the internal pulse generator as previously mentioned. While not preferred, the reference electrode RE can be placed in the left ventricle (FIG. 11) (or in the tissue of the free wall FW as shown in phantom lines in FIG. 11), on the epicardial surface (FIG. 12) or in the coronary sinus CS (FIG. 13).

Positioning the reference electrode RE relative to the heart can affect the distortion of the field in the area of the left ventricle free wall FW subject to pacing. Particularly for a subcutaneously placed reference electrode (which is preferred to minimize the invasive nature of the procedure), the electrical conduction path from the right ventricle RV to the reference electrode will vary considerably between patients.

Figure 15:
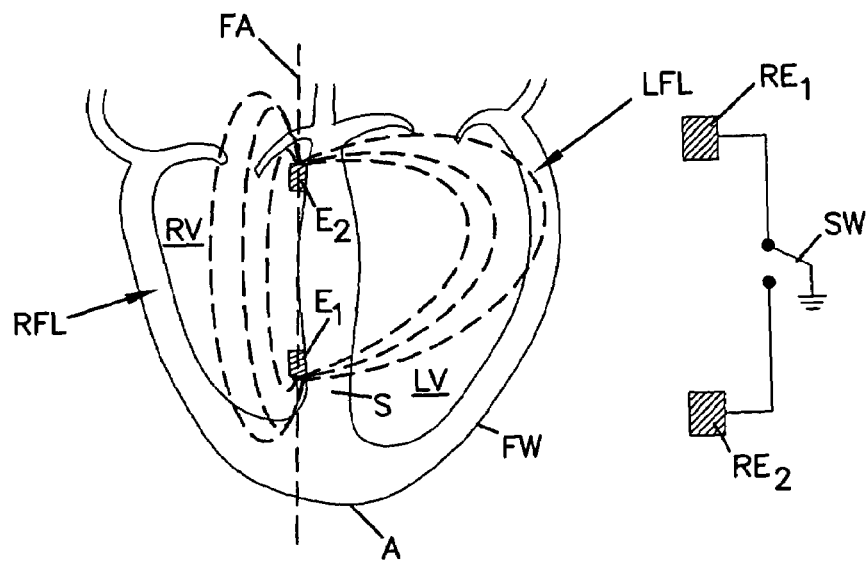
FIG. 15 shows a field distorted towards an upper end of the free wall in response to a reference electrode in a first position.
Figure 16:
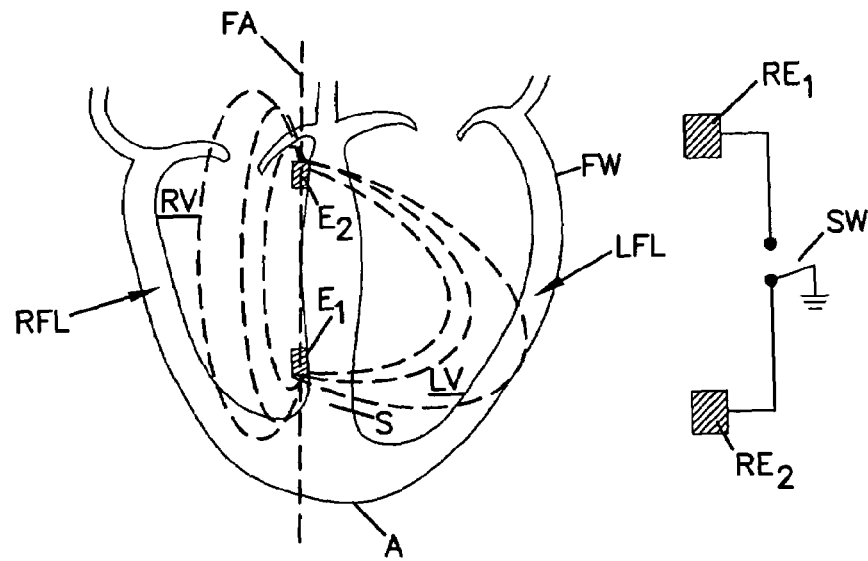
FIG. 16 is the view of FIG. 15 with a reference electrode switched to a second position.

Also, the direction of field distortion may alter the region of the left ventricle LV subject to pacing. For example, FIG. 15 illustrates the reference electrode $RE_1$ placed high relative to the heart resulting in a distortion of the field toward the upper end of the left ventricle septum and free wall FW. FIG. 16 illustrates placement of a reference electrode $RE_2$ lower relative to the heart and to deflect the intensity of the field toward the lower end of the left ventricle septum and free wall FW.

While the reference electrode could be a single electrode, multiple electrodes could be provided for subcutaneous placement and each connected by a switch circuitry SW of the implantable pulse generator as illustrated in FIGS. 15 and 16. The patient's response can be noted with each of the several reference electrodes $RE_1$, $RE_2$ separately connected to the ground or housing of the implantable pulse generator. The patient can then be treated with the electrode showing the most effectiveness for the particular patient. Further, over time, a patient's response may change and the implantable pulse generator can be reprogrammed to select any one of the other reference electrodes as the switched electrode.

Figure 7:
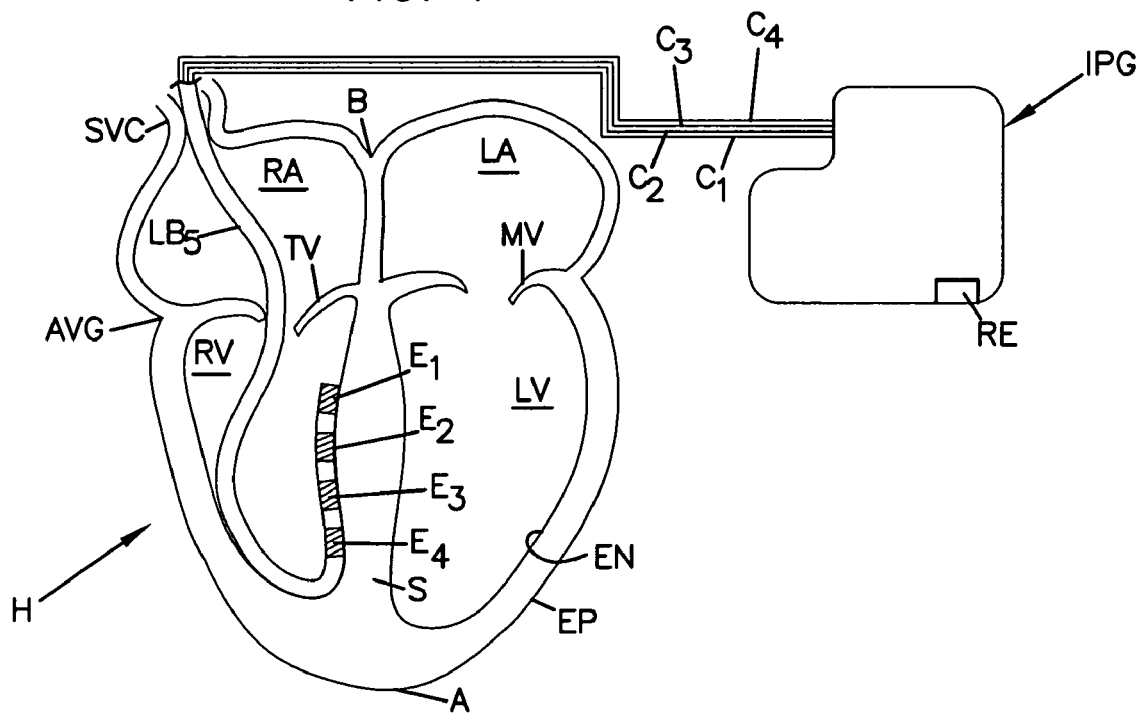
FIG. 7 is the view of FIG. 4 showing the lead of FIG. 4 with multiple electrodes urged against the septal wall.
Figure 7A:
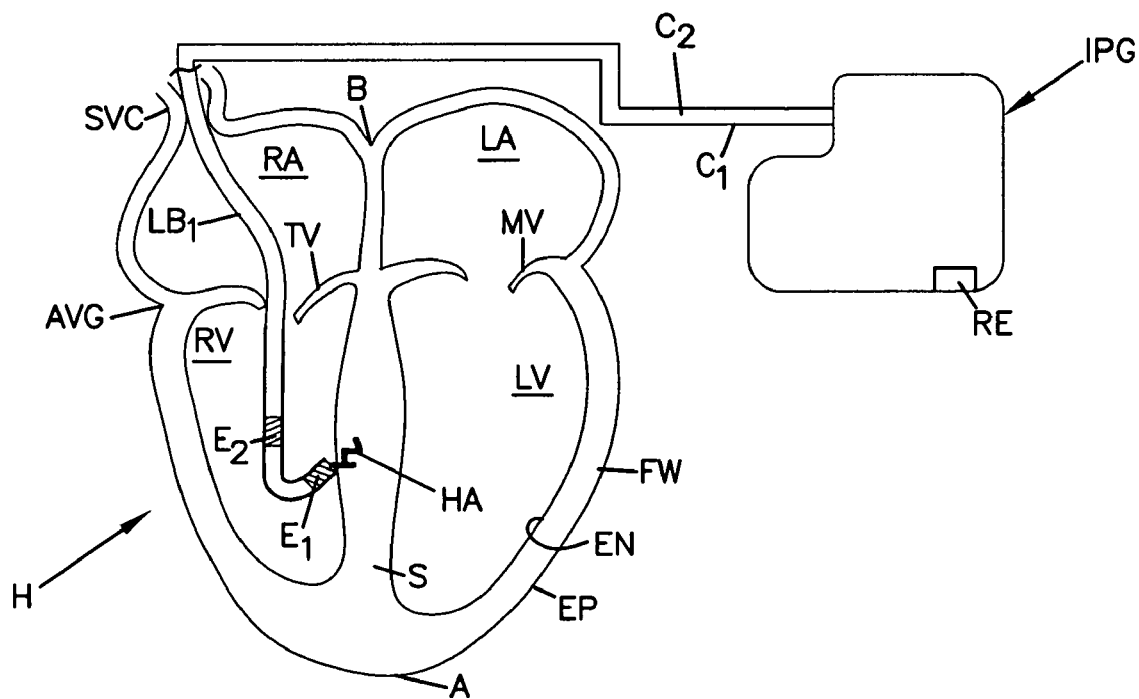
FIG. 7A is the view of FIG. 1 showing a conventional active fixation lead with a helix for attachment of the tip electrode to a septal wall.
Figure 7B:
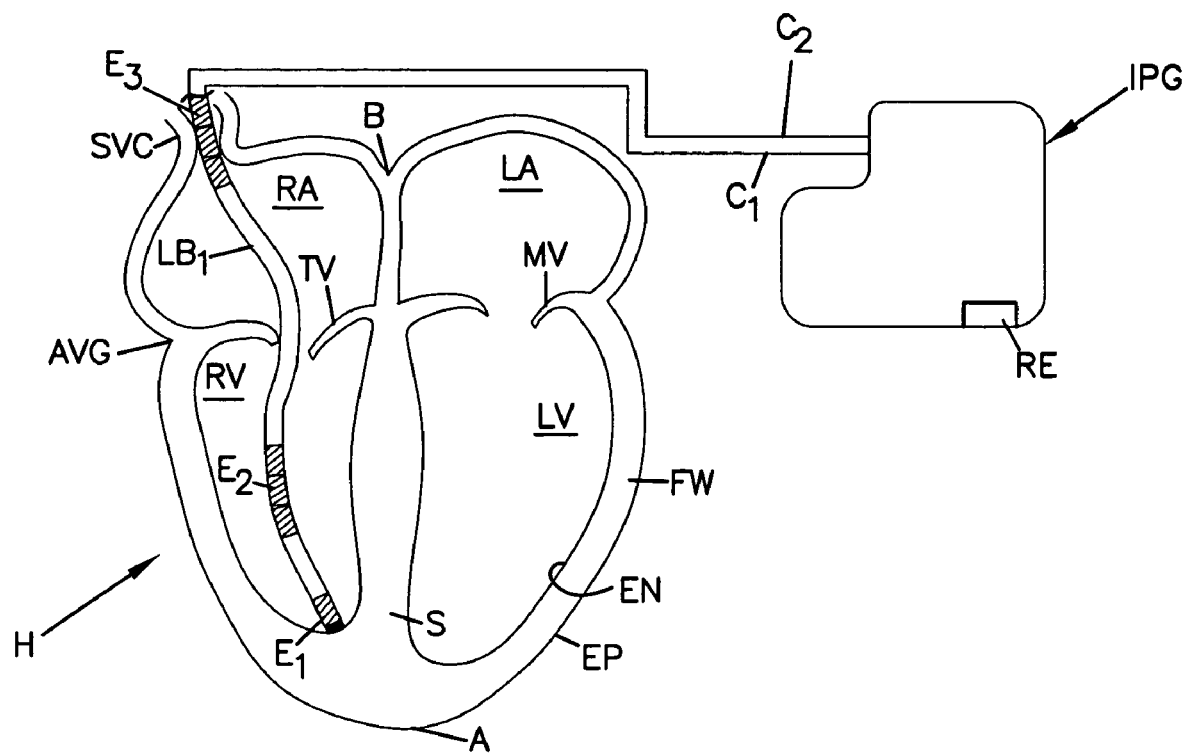
FIG. 7B is the view of FIG. 1 showing a shocking electrode.

In addition, the catheter $LB_5$ within the right ventricle can have multiple electrodes along its length (as shown in FIG. 7). Individual pairs of these electrodes $E_1$-$E_4$ can be switched on or off over time so that the appropriate pair of electrodes within the right ventricle is selected for optimized left ventricular pacing.

Figure 19:
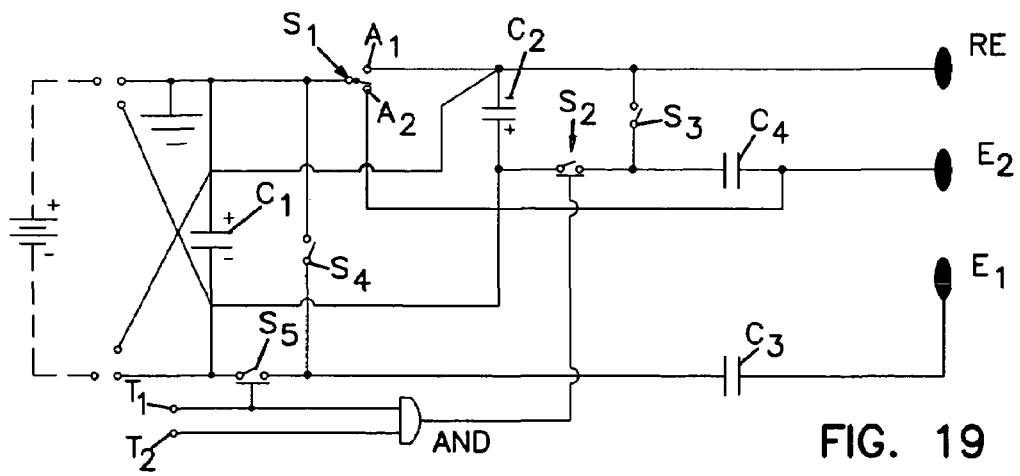
FIG. 19 is an electrical schematic for a portion of a pacing output desired in a pulse generator with programmable pacing configurations.

FIG. 19 illustrates a representative circuit in schematic format for a portion of a cardiac stimulation pulse generator that is capable of providing pacing output for either the conventional design or the present invention. The circuit of FIG. 19 could be for an implantable pacemaker or any external stimulation system for diagnostic or therapeutic use.

The stimulation device has three output terminals that are connected to three electrodes $E_1$, $E_2$, RE in the body. Electrodes $E_1$, $E_2$ are positioned in the right ventricle RV with it being preferred that at least one of these electrodes be in direct contact with the septum S.

The reference electrode RE is an indifferent electrode which can be connected electronically to the housing of the implantable pulse generator IPG. The reference electrode RE may be an electrode directly on the implantable pulse generator or any other electrode for placement inside or outside of the heart as described above.

Figure 17:
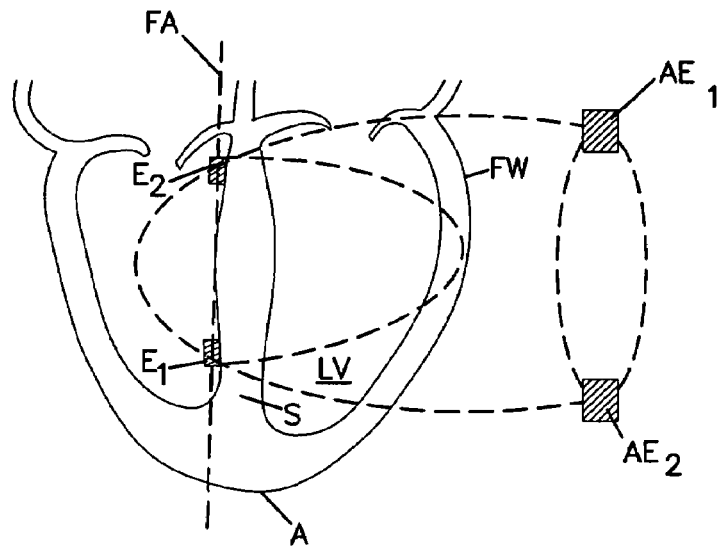
FIG. 17 is the view of FIG. 15 with a reference electrode replaced by two polarized electrodes.

In the preferred embodiment, the reference electrode is grounded to the housing of the implantable pulse generator. FIG. 17 illustrates an alternative embodiment where the reference electrode includes two active electrodes $AE_1$, $AE_2$ external to the heart. The active electrodes $AE_1$, $AE_2$ are paced with pulsed waveforms which are polar opposites of the waveforms on electrodes $E_1$, $E_2$. This creates dual uni-polar field $F_1$, $F_2$ in addition to the left field lines LFL previously described.

In the Figure, the amplitude of the waveforms from FIG. 18 (or other waveform as described) is shown in phantom lines as the battery voltage applied to the four poles on the left of FIG. 19 to charge the two pacing capacitors $C_1$ and $C_2$. Details of the charging circuitry as well as other controlling circuitry for pacing and sensing are omitted for ease of illustration, but should be customary to those skilled in the art. Only capacitor $C_1$ needs to be charged for the conventional pacing output, whereas both C1 and C2 need to be charged for the present invention. Capacitor $C_3$ and $C_4$ are for the pacing output coupling to the patient. For ease of illustration and explanation, the output waveform from FIG. 18 with the same amplitude and simultaneous timing is assumed for the design schematic in FIG. 19. A switch $S_1$ permits selection between unipolar conventional pacing and pacing according to the present invention (by contact with switch pole $A_1$) or bi-polar conventional pacing (by contact with switch pole $A_2$). Selection between conventional pacing or the present invention is made by applying a digital signal with the timing information as shown in FIG. 18 to either $T_1$ or $T_{1\ and\ T2}$, namely to either toggle the switch $S_5$ or $S_2$ and $S_5$ simultaneously). An AND gate is used to allow the close of the switch $S_2$ only for pacing according to the present invention. Switches $S_3$ and $S_4$ permit re-neutralizing the pacing charges at the patient-electrode interface.

As is customary with implantable pulse generators, the device may be programmable to achieve either conventional bipolar or unipolar stimulation or to achieve the stimulation of the present invention through an external programmer or controlled automatically by the device. The selection can be based on user preference or be driven by physiological factors such as widths of the patient's QRS complex or the conduction interval between the stimulus to a far away region in the heart. In addition switching between the pacing of the present invention and conventional pacing can also be determined by the percentage of pacing with a preference for a higher percentage with the pacing of the present invention. Further, the switching from the conventional pacing to the present invention pacing can be used when there exists an exit block or the pacing electrode is located in infracted myocardium when conventional pacing can not effect the depolarization of the myocardium at the high output level. The automatic determination can be effected through the deployment of any automatic capture detection technology that exists in the prior art. Additionally, wireless network enabled switching function for therapy optimization can also be implemented with the present invention. In such case, certain patient physiologic data are gathered by the implantable device and sent to a remote server/monitor through a wireless communication network.

FIG. 18 illustrates a preferred waveform with electrodes $E_1$, $E_2$ being simultaneously pulsed with opposite polarity. FIG. 18A illustrates waveforms $W_1'$, $W_2'$ of similar structure to the waveforms of FIG. 18 but slightly out of phase to present a partial overlap duration DO. With FIG. 18A at least a portion of time includes a monopolar pacing from individual ones of the electrodes $E_1$, $E_2$ to the reference electrode RE. This pacing creates out of phase monopolar fields $F_1$, $F_2$ as illustrated in FIG. 18B. While the amplitudes of the two waveforms are shown equal, they need not be equal in practice.

The present invention can also be extended to the defibrillation therapy where high-energy pulses with various waveforms are delivered through electrode systems to treat tachycardia and fibrillation (both atrium and ventricle). The present invention is believed to be able to achieve lower defibrillation threshold due to better distribution of the electrical field, causing higher voltage gradient at least in certain parts of the heart compared to that by the conventional defibrillation configuration as seen in FIG. 7B. Additionally, the present invention can be used to perform anti-tachy pacing where faster than conventional pacing pulse sequences are used to stop certain tachyarrhythmia. The present invention is believed to be advantageous due to the wider coverage of the electrical field and the capability of capturing special conductions system in the heart (both atrium and ventricle).

Figure 20:
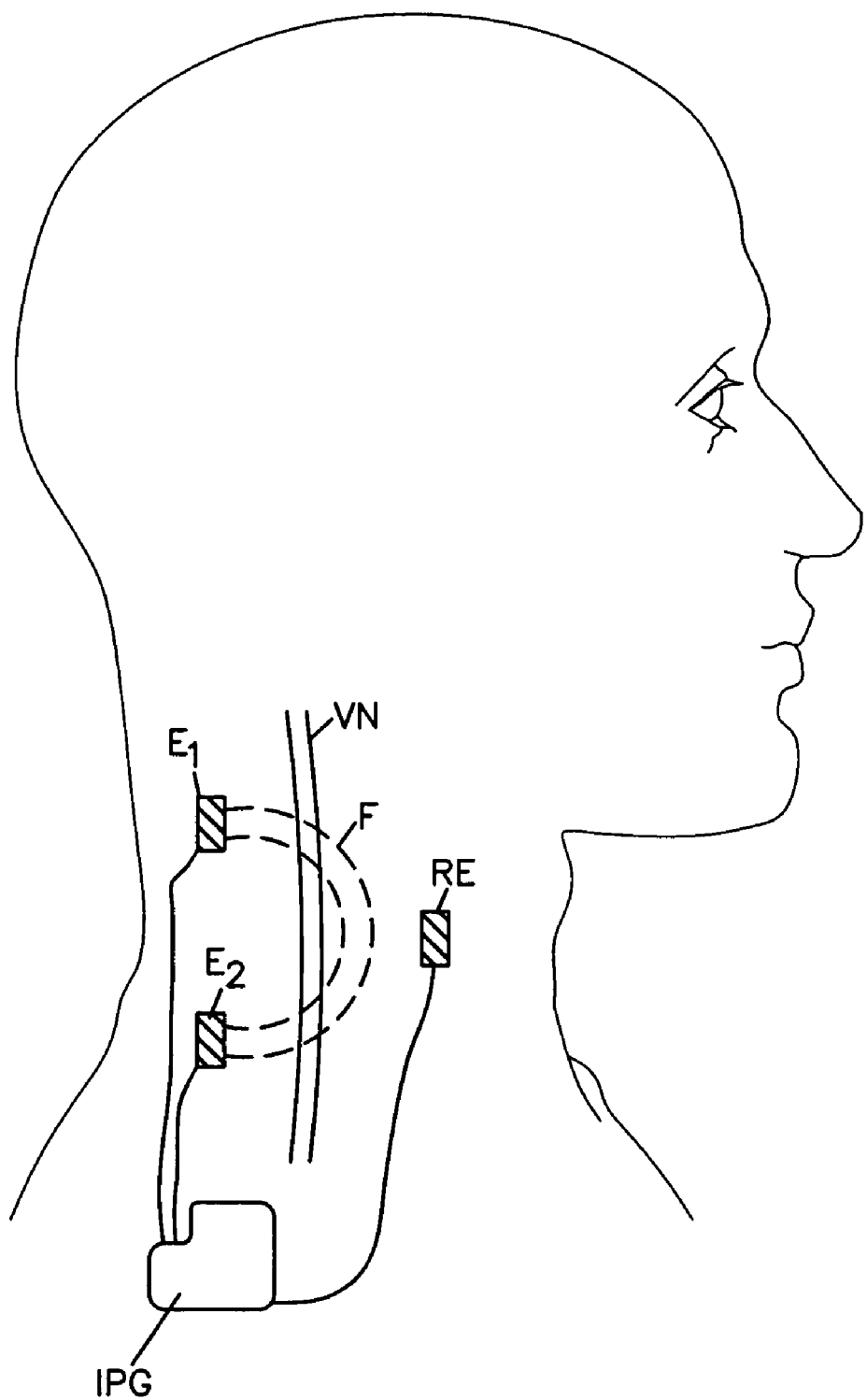
FIG. 20 is a side elevation view of a patient's head and neck showing application of the present invention directed to applying a pacing signal to a vagus nerve.

While cardiac applications are a most preferred embodiment, the present application is applicable to other therapies where high current density spot(s) away from the electrodes are beneficial for stimulating the target, including but not limited to nerves, muscle, gastric and intestine system, and cortex). For example, U.S. Pat. No. 5,299,569 to Wernicke et al. issued Apr. 5, 1994 (and incorporated herein by reference is one of a number of patents assigned to Cyberonics, Inc. describes pacing the vagus nerve to treat a wide variety of disorders. Pacing electrodes are applied directly to the vagus nerve in, for example, the neck. Application of an electrode directly to the vagus nerve creates risk of mechanical injury (e.g., pressure necrosis) to the nerve. FIG. 20 illustrates use of the present invention in such application. Electrodes $E_1$, $E_2$ are placed subcutaneously near (trancutaneously or transvenously coupled) but not on the vagus nerve VN in the neck. A reference electrode RE is placed subcutaneously (trancutaneously or transvenously coupled) on an opposite side of the nerve VN. The electrodes $E_1$, $E_2$ and RE are connected to a pulse generator IPG. With signals as described above, the resulting field F captures the vagus nerve. The signals may be selected to have amplitude, frequency and other parameters as more fully described in the '569 patent. It will be appreciated that other alternative examples of using the present invention to pace an organ or the nerve will occur to one of ordinary skill in the art with the benefit of the teachings of the present invention.

It has been shown how the objects of the invention have been achieved in a preferred embodiment. Modifications and equivalents of the disclosed concepts are intended to be included within the scope of the claims appended hereto.

What is claimed is:

1. A method for treating a condition of a heart of a patient, said method comprising:
   placing a first electrode and a second electrode in a right ventricle of the heart;
   placing a reference electrode within said patient and internal or external to the heart;
   generating a pacing signal including a first signal component, a second signal component and a reference component with said first and second signal components having opposite polarity and with both of said first and second components having a potential relative to said reference component; and
   transmitting said first component to said first electrode, said second component to said second electrode and said reference component to said reference electrode and, in response thereto, capturing a contraction of a left ventricle of the heart where the contraction is a more rapid and uniform activation.

2. A method according to claim 1 wherein the step of transmitting field lines between the first electrode and the second electrode and wherein the method further comprises a step of securing at least one of said first and second electrodes to a septum of said heart and sufficiently near the His bundle of the heart to allow the field lines to stimulate the His Bundle thereby creating the more rapid and uniform activation and wherein the more rapid and uniform activation treats a conduction abnormality.

3. A method according to claim 1 further comprising a step of positioning said reference electrode to bias a field between said first and second electrodes toward a region that allows more synchronous contraction of the left ventricle to treat bundle branch block.

4. A method according to claim 1 further including a step of placing one or more additional reference electrodes connected by a switch to said reference component.

5. A method according to claim 1 further including the step of positioning said reference electrode within said patient body to distort a field from said first and second electrodes to said left ventricle, and wherein the first and second signal components are less than 20 Volts.

6. A method according to claim 1, wherein the step of placing a first electrode and a second electrode in a right ventricle of said heart includes placement of at least the first electrode near the tricuspid valve.

7. A method according to claim 1, wherein the reference electrode is located proximate to the signal generator and distal from the heart.

8. An apparatus for treating a condition of a heart of a patient, said apparatus comprising:
   a first electrode and a second electrode each adapted for placement in a right ventricle of said heart;
   a reference electrode for placement within said patient and internal or external to said heart;
   a signal generator for generating a pacing signal including a first signal component, a second signal component and a reference component with said first and second signal components having opposite polarity and with both of said first and second components having a potential relative to said reference component; and
   said signal generator coupled to said electrodes for transmitting said first component to said first electrode, said second component to said second electrode and said reference component to said reference electrode, said first and second components to deliver voltages for capturing a contraction of a left ventricle of the heart where the contraction is a more rapid and uniform activation.

9. An apparatus according to claim 8 wherein said signal generator is configured for transmitting by wireless transmission.

10. An apparatus according to claim 8 wherein said signal generator further includes circuitry for switching from said pacing to a second pacing mode.

11. An apparatus according to claim 8 further comprising multiple reference electrodes with a switch for selecting a particular one of said multiple reference electrodes to be connected to said reference component.

12. An apparatus according to claim 8 further comprising a lead with at least one electrode adapted to be placed in said atrium to facilitate atrial-ventricular sequential pacing.

13. An apparatus according to claim 8 further comprising a lead with an electrode adapted to be placed on said left ventricle and energized with a pacing/sensing circuitry.

14. An apparatus according to claim 8 further comprising a defibrillation lead system with at least one large shocking electrode and circuitry for energizing the said defibrillation electrode system (including, but not limited to the shocking electrode and the IPG housing) for defibrillation therapy.

15. An apparatus according to claim 8 further comprising a plurality of additional electrodes adapted for placement in said right ventricle, said signal generator including circuitry for selectively connecting one of said plurality to said first component and a second of said plurality to said second component.

16. An apparatus according to claim 8 including at least two reference electrodes.

17. An apparatus according to claim 8 wherein the signal generator is coupled to said electrodes for transmitting said first component to said first electrode, said second component to said second electrode and said reference component to said reference electrode, for delivering the pacing signal to a selected area near or at the septum for treating a bundle branch block.

18. A method comprising:

in a patient's heart manifesting a condition involving mechanical asynchrony and a conduction block in a bundle branch, placing a primary electrode in the right ventricle;

securing the primary electrode to the septum of the heart to treat the condition; and generating a pacing signal for presentation to the right ventricle by the primary electrode with the pacing signal presenting a voltage on the primary electrode relative to a reference voltage, and causing activation of the normal electrical conduction in the heart and therein treating the mechanical asynchrony by improving the coordinated contraction of the ventricles and free wall of the left ventricle.

19. The method of claim 18, wherein the step of generating a pacing signal includes generating a pulse of less than about 20 Volts.

20. The method of claim 18, wherein the step of securing the primary electrode includes securing the primary electrode near the tricuspid valve of the right ventricle.

* * * * *